United States Patent
Ben-Haim et al.

(10) Patent No.: US 6,321,109 B2
(45) Date of Patent: *Nov. 20, 2001

(54) CATHETER BASED SURGERY (75) Inventors: Shlomo Ben-Haim, Haifa; Maier Fenster, Petach Tikva, both of (IL)

(73) Assignee: Biosense, Inc., New Brunswick, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/117,804
(22) PCT Filed: Feb. 14, 1997
(86) PCT No.: PCT/IL97/00059
§ 371 Date: Dec. 29, 1998
§ 102(e) Date: Dec. 29, 1998
(87) PCT Pub. No.: WO97/29701
PCT Pub. Date: Aug. 21, 1997

Related U.S. Application Data (60) Provisional application No. 60/011,721, filed on Feb. 15, 1996.

(51) Int. Cl.⁷ .................................................. A61B 17/22
(52) U.S. Cl. ........................... 600/424; 601/2; 601/4; 604/22
(58) Field of Search ............................ 600/424, 437, 600/439, 458, 464, 466, 462; 424/9.5; 604/22; 601/4, 2

(56) References Cited

U.S. PATENT DOCUMENTS

| | | |
|---|---|---|
| 3,644,825 | 2/1972 | Davis, Jr. et al. ........... 324/41 |
| 3,868,565 | 2/1975 | Kuipers ...................... 324/34 R |
| 4,017,858 | 4/1977 | Kuipers ...................... 343/100 R |

(List continued on next page.)

FOREIGN PATENT DOCUMENTS

| | | | |
|---|---|---|---|
| 0 467 031 A | 1/1992 | (EP) . | |
| 0 732 106A2 | * 9/1996 | (EP) ..................... | A61K/49/00 |
| WO 94/00050 | 1/1994 | (WO) . | |
| WO 94/04938 | 3/1994 | (WO) . | |
| WO 94/06349 | 3/1994 | (WO) . | |
| WO 94/23647 | 10/1994 | (WO) . | |
| WO 94/28782 | 12/1994 | (WO) . | |
| WO 95/05773 | 3/1995 | (WO) . | |
| WO 95/07657 | 3/1995 | (WO) . | |
| WO 95/09562 | 4/1995 | (WO) . | |
| WO 95/10226 | 4/1995 | (WO) . | |
| WO 95/19738 | 7/1995 | (WO) . | |

(List continued on next page.)

OTHER PUBLICATIONS

"Effects of laser irradiation delivered by flexible fiberoptic system on the left ventricular internal myocardium" American Heart Journal, Sep. 1983, pp. 587–590.

Dorothy Bonn, "High–Power laser help the Ischaemic Heart", The Lancet, vol. 348 (Jul. 13, 1996) p. 118.

Mahmood Mirhoseini et al., "Transmyocardial Laser Revascularization: A Review" Journal of Clinical Laser Medicine & Surgery. vol. 11(1993) pp. 15–19.

*Primary Examiner*—Marvin M. Lateef
*Assistant Examiner*—Eleni Mantis Mercader
(74) *Attorney, Agent, or Firm*—Louis J. Capezzuto (57) ABSTRACT

A method of excavating tissue in the body, including bringing a catheter (60) to a location, injecting microbubbles (84) at the location and causing cavitation of tissue (76) at the location using ultrasound. Preferably, the microbubbles (84) are injected directly into the tissue, such as by using a hollow needle (62). Alternatively, microbubbles (84) are injected into the vascular bed of the tissue at the location, so that the capillaries (86) are infused with microbubbles (84).

6 Claims, 8 Drawing Sheets

U.S. PATENT DOCUMENTS

| | | | |
|---|---|---|---|
| 4,054,881 | 10/1977 | Raab | 343/112 R |
| 4,560,930 | 12/1985 | Kouno | 324/207 |
| 4,570,354 | 2/1986 | Hindes | 33/534 |
| 4,592,356 | 6/1986 | Gutierrez | 128/339 |
| 4,613,866 | 9/1986 | Blood | 343/448 |
| 4,642,786 | 2/1987 | Hansen | 364/559 |
| 4,651,436 | 3/1987 | Gaal | 33/533 |
| 4,671,292 | 6/1987 | Matzuk . | |
| 4,710,708 | 12/1987 | Rorden et al. | 324/207 |
| 4,788,987 | 12/1988 | Nickel | 128/777 |
| 4,849,692 | 7/1989 | Blood | 324/208 |
| 4,869,238 | 9/1989 | Opie et al. | 128/6 |
| 4,905,698 | 3/1990 | Strohl, Jr. et al. | 128/653 R |
| 4,917,095 | 4/1990 | Fry et al. | 128/660.03 |
| 4,921,482 | 5/1990 | Hammerslag et al. | 604/95 |
| 4,931,059 | 6/1990 | Markham | 606/185 |
| 4,945,305 | 7/1990 | Blood | 324/207.117 |
| 5,002,137 | 3/1991 | Dickinson et al. | 175/19 |
| 5,042,486 | 8/1991 | Pfeiler et al. | 128/653 R |
| 5,059,197 | 10/1991 | Urie et al. | 604/164 |
| 5,078,144 | 1/1992 | Sekino et al. | 128/660.03 |
| 5,099,845 | 3/1992 | Besz et al. | 128/653.1 |
| 5,125,924 | 6/1992 | Rudko | 606/12 |
| 5,125,926 | 6/1992 | Rudko et al. | 606/19 |
| 5,158,084 | 10/1992 | Ghiatas | 128/657 |
| 5,172,056 | 12/1992 | Voision | 324/207.17 |
| 5,195,540 | 3/1993 | Shiber | 128/898 |
| 5,195,968 | 3/1993 | Lundquist et al. | 604/95 |
| 5,197,482 | 3/1993 | Rank et al. | 128/749 |
| 5,211,165 | 5/1993 | Dumoulin et al. | 128/653.1 |
| 5,215,680 | 6/1993 | D'Arrigo | 252/307 |
| 5,217,484 | 6/1993 | Marks | 606/200 |
| 5,234,426 | 8/1993 | Rank et al. | 606/1 |
| 5,251,635 | 10/1993 | Dumoulin et al. | 128/653.1 |
| 5,253,647 | 10/1993 | Takahashi et al. | 128/653.1 |
| 5,255,680 | 10/1993 | Darrow et al. | 128/653.1 |
| 5,265,610 | 11/1993 | Darrow et al. | 128/653.1 |
| 5,267,960 | 12/1993 | Hayman et al. | 604/106 |
| 5,273,025 | 12/1993 | Sakiyama et al. | 128/6 |
| 5,275,166 | 1/1994 | Vaitekunas et al. | 128/660.03 |
| 5,295,484 | 3/1994 | Marcus et al. | 128/660 |
| 5,295,486 | 3/1994 | Wollschager et al. | 128/661.01 |
| 5,301,682 | 4/1994 | Debbas | 128/737 |
| 5,309,913 | 5/1994 | Kormos et al. | 128/653 |
| 5,325,873 | 7/1994 | Hirschi et al. | 128/899 |
| 5,368,564 | 11/1994 | Savage | 604/95 |
| 5,368,592 | 11/1994 | Stern et al. | 606/33 |
| 5,373,849 | 12/1994 | Maroney et al. | 128/662 |
| 5,375,596 | 12/1994 | Twiss et al. | 128/653.1 |
| 5,377,678 | 1/1995 | Dumoulin et al. | 128/653.1 |
| 5,380,316 | 1/1995 | Aita et al. | 606/7 |
| 5,383,454 | 1/1995 | Bucholz | 128/653.1 |
| 5,383,874 | 1/1995 | Jackson et al. | 606/1 |
| 5,383,923 | 1/1995 | Webster, Jr. | 607/125 |
| 5,385,148 | 1/1995 | Lesh et al. | 128/662.06 |
| 5,389,096 | 2/1995 | Aita et al. | 606/15 |
| 5,391,199 | 2/1995 | Ben Haim | 607/122 |
| 5,403,356 | 4/1995 | Hill et al. | 607/14 |
| 5,404,297 | 4/1995 | Birk et al. | 362/421 |
| 5,409,004 | 4/1995 | Sloan | 128/657 |
| 5,423,321 | 6/1995 | Fontenot | 128/664 |
| 5,425,367 | 6/1995 | Shapiro et al. | 128/653 |
| 5,425,382 | 6/1995 | Golden et al. | 128/899 |
| 5,429,132 | 7/1995 | Guy et al. | 128/653.1 |
| 5,431,168 | 7/1995 | Webster, Jr. | 128/658 |
| 5,433,198 | 7/1995 | Desai | 128/642 |
| 5,437,277 | 8/1995 | Dumoulin et al. | 128/653.1 |
| 5,443,489 | 8/1995 | Ben-Haim | 607/115 |
| 5,450,846 | 9/1995 | Goldreyer | 128/642 |
| 5,465,717 | 11/1995 | Imran et al. | 128/642 |
| 5,471,982 | 12/1995 | Edwards et al. | 128/642 |
| 5,471,988 | 12/1995 | Fujio et al. | 128/660.03 |
| 5,480,422 | 1/1996 | Ben-Haim | 69907/122 |
| 5,483,951 | 1/1996 | Frassica et al. | 600/104 |
| 5,487,391 | 1/1996 | Panescu | 128/699 |
| 5,538,008 | 7/1996 | Crowe | 128/751 |
| 5,549,112 | * 8/1996 | Cockburn et al. | 128/662.05 |
| 5,554,152 | 9/1996 | Aita et al. | 606/7 |
| 5,555,883 | 9/1996 | Avitall | 128/642 |
| 5,558,091 | 9/1996 | Acker et al. | 128/653.1 |
| 5,558,092 | 9/1996 | Unger et al. | 128/660.03 |
| 5,577,502 | 11/1996 | Darrow et al. | 128/653.1 |
| 5,588,432 | 12/1996 | Crowley | 128/660.03 |
| 5,617,857 | 4/1997 | Chader et al. | 128/653.1 |
| 5,622,169 | 4/1997 | Golden et al. | 128/653.1 |
| 5,715,822 | 2/1998 | Watkins et al. | 128/653.5 |
| 5,729,129 | 3/1998 | Acker | 324/207.12 |
| 5,879,305 | * 3/1999 | Yock et al. | 600/462 |
| 6,018,676 | * 1/2000 | Davis et al. | 600/431 |

FOREIGN PATENT DOCUMENTS

| | | |
|---|---|---|
| WO 96/05768 | 2/1996 | (WO) . |
| WO 96/41119 | 12/1996 | (WO) . |
| WO 97/03609 | 2/1997 | (WO) . |
| WO 97/29678 | 8/1997 | (WO) . |
| WO 97/29679 | 8/1997 | (WO) . |
| WO 97/29683 | 8/1997 | (WO) . |
| WO 97/29684 | 8/1997 | (WO) . |
| WO 97/29685 | 8/1997 | (WO) . |
| WO 97/29701 | 8/1997 | (WO) . |
| WO 97/29709 | 8/1997 | (WO) . |
| WO 97/29710 | 8/1997 | (WO) . |
| WO 97/29803 | 8/1997 | (WO) . |
| WO 97/32179 | 9/1997 | (WO) . |

* cited by examiner

CATHETER BASED SURGERY

RELATED APPLICATION

This application claims the benefit of U.S. Provisional application No. 60/011,721, titled "Catheter Based Surgery" and filed Feb. 15, 1996, the disclosure of which is incorporated herein by reference. This application is related to the following PCT applications filed on even date as the instant application by (a) applicant Biosense Inc.: "Medical Procedures and Apparatus Using Intrabody Probes", filed in the U.S. receiving office and "Locatable Biopsy Needle" and "Intrabody Energy Focusing", and (b) applicant Victor Spivak: "Multi-Element Energy Focusing", all three filed in the Israeli receiving Office. All the PCT applications designate, inter alia, the U.S.

FIELD OF THE INVENTION

The present invention relates to the field of minimally invasive surgery and in particular to performing surgery using catheters.

BACKGROUND OF THE INVENTION

Surgical intervention is a traumatic experience to the patient. Many surgical procedures require cutting through multiple layers of body tissues including fat, muscles and, sometimes, bones to provide a pathway to a lesion being treated. For example, in a standard appendix operation, the abdominal muscles are cut to expose the appendix. The cut muscles typically take much longer to heal than the injury caused by removing the appendix. In a newer appendix removal operation, using a laproscope, only a single hole is punched through the abdomen to reach the appendix. This type of surgery is part of a growing field that is known as minimally invasive medical procedures.

Minimally invasive medical procedures aim to minimize the trauma to the patient to the minimum necessary for the required therapeutic action. Since most of the trauma in surgery is caused by entering the body, several devices have been developed which can operate within the body and which have a minimal traumatic effect on the body when entering it. For example, endoscopes, which enter through one of the body orifices, for operating in the GI tract, laproscopes which are punched directly into the soft tissue of the body, orthoscopes for operating in joint capsules, vascular catheters for operating in the vascular system and special catheters for the urinary tract. In general, minimally invasive medical procedures are faster, less traumatic to the patient and safer than standard invasive medical procedures.

One example of a minimally invasive procedure is dissolution of a thrombosis using an catheter. Acute myocardial infarcts (heart attacks) and strokes are usually caused by a thrombosis which lodges in a narrowed portion of a blood vessel, blocking it and reducing the supply of oxygen to tissues. In many cases some tissue damage can be averted by promptly removing the thrombosis. In a typical procedure, a catheter is guided through the vascular system to the proximity of the thrombosis. A fibrin dissolving material, such as streptokinase or t-PA enzymes, is injected into the blood vessel and dissolves the thrombosis. In alternative procedures, the thrombosis is cut with a laser beam mounted on the catheter, disintegrated using high power ultrasound channeled through the catheter or compressed against the vessel wall using a balloon. In another minimally invasive medical procedure, a stent is placed in an aneurysm. The stent causes clotting of blood surrounding the stent, so the aneurysm is effectively sealed using the stent. Another type of minimally invasive procedure uses a catheter to inject anti-cancer drugs in proximity to tumors in the brain.

U.S. Pat. No. 4,917,095, the disclosure of which is incorporated herein by reference, describes a minimally invasive procedure for removing gallstones. Gallstones may be formed of two layers, a thin, hard, outer layer which can be disintegrated using an externally generated sonic shockwave and a thick, soft inner layer which can be disintegrated using certain chemicals. In the '095 patent, a catheter or endoscope is brought into the bile ducts and a chemical, which dissolves gallstones, is introduced into the gallbladder. The outer shell of the gallstones is shattered using a sonic shockwave so that the dissolving chemical can disintegrate the soft inner layer. In other procedures, an anti-cancer drug, which is locally injected using a catheter, is made more potent by heating the area using focused ultrasound or microwaves.

U.S. Pat. No. 5,215,680 to D'Arrigo, the disclosure of which is incorporated herein by reference, discloses a method of producing medical-grade lipid coated microbubbles. In addition, the '680 patent discloses that such microbubbles naturally cross capillary walls at most types of tumors. One suggested method of treating tumors is to inject such microbubbles into the blood stream, wait for microbubbles to accumulate in the tumor and irradiate the tumor with high power ultrasound which induces cavitation of the microbubbles. This cavitation completely destroys the tissue in which the microbubbles are accumulated. Another suggested method of tumor destruction is to create microbubbles which encapsulate anti-cancer drugs. Again, when these microbubbles are injected into the bloodstream, the microbubbles accumulate in the tumor, and, after a while, release their anti-cancer drugs.

One method of providing high powered ultrasound at an intra-body location is using focused ultrasound. Usually, ultrasound is focused using a phased array of transmitters. In some systems only the depth of the focal point is controllable, while in others, the focal point can be moved in a plane parallel to the phased array by suitably operating the array. Focused ultrasound, at a sufficient energy density, is used to destroy tissue, especially tumors. However, focused ultrasound has two main limitations. First, the achievable focal spot size is not much smaller than 5 millimeters. Second, the exact location of the focal spot is difficult to determine ahead of time. The acoustic velocity in soft tissue is dependent on the tissue type and, as a result, refraction effects move the focal spot and diffuse it.

One medical procedure, is a liver bypass. Patients which have advanced chirosis of the liver suffer, as a result of blockage of the portal vein, from elevated venous blood pressure, which may cause fatal GI bleeding. In this experimental procedure, a shunt is created between the hepatic vein and the portal vein in the liver to bypass most of the liver. Thus, the venous blood pressure is reduced and GI bleeding eliminated. To create the shunt, a catheter is is inserted into either the portal or the hepatic vein, and a needle is used to probe for the other vein. Since the needle is hollow, when the other vein is found, blood flows through the needle. A stent is guided along the needle to connect the two veins. This procedure is performed using a fluoroscope and is very lengthy, so the amount of radiation exposure of the patient and the surgeon is considerable.

Another experimental medical procedure can be used to aid perfusion in an ischemic heart. This procedure is more fully described in U.S. Pat. No. 5,380,316, the disclosure of which is incorporated herein by reference. In this procedure, a laser tipped catheter is brought into contact with an ischemic portion of the heart and holes, which perforate the heart wall, are drilled into the wall of the heart using the laser. After a short time, perfusion in the ischemic portion improves. It is not at this time clear whether the heart is directly perfused via these holes or whether the trauma caused by drilling the holes encourages the formation of new capillaries. A main concern with this procedure is the perforation of the heart.

SUMMARY OF THE INVENTION

It is an object of some aspects of the present invention to provide apparatus and methods for performing controlled tissue destruction in the body using a minimally invasive medical probe, such as a catheter.

It is another object of some aspects of the present invention to provide minimally invasive therapeutic procedures.

Some preferred embodiments of the present invention seek to obtain these objectives by providing means and apparatus for performing surgery in the human body using catheters. Preferably, the catheters have a position detecting sensor mounted thereon. Surgical procedures according to some preferred embodiments of the present invention coordinate the activities of several catheters using position detection of the catheters.

One advantage of catheter based surgery is that catheter can advantageously be used to perform functional mapping of the diseased tissue. Using catheter-based functional mapping, it is easier to determine the extent of the diseased tissue and to treat the diseased tissue during the same procedure.

There is therefore provided in accordance with a preferred embodiment of the invention, an excavating probe including, a probe body having a distal tip, a position sensor which determines the position of the tip and a source of laser radiation for excavating adjacent to the tip.

There is therefore provided in accordance with another preferred embodiment of the invention an excavating probe including, a probe body having a distal tip, a position sensor which determines the position of the tip and a source of microbubbles at the tip. Preferably, the source of microbubbles includes a hollow needle which injects the microbubbles into tissue adjacent the tip. Additionally or alternatively, the probe includes an ultrasonic imager which views regions adjacent said tip. Additionally or alternatively the position sensor includes an orientation sensor which determines the orientation of the tip of the probe.

There is also provided in accordance with a preferred embodiment of the invention a method of minimally invasive surgery including, bringing a first probe, having a position sensor, into a hepatic vein, finding the hepatic vein using a imager, determining the relative positions of the probe and the vein using the position sensor, tunneling from the hepatic vein to the portal vein and installing a stent between the two veins. Preferably, tunneling includes excavating tissue between the portal and the hepatic veins. Alternatively, tunneling includes forcing one of the probes through the tissue between the veins.

There is also provided in accordance with another preferred embodiment of the invention a method of perfusing heart muscle, including, bringing a probe into contact with a location at an ischemic portion of a heart, excavating an evacuation at the location and repeating the method at a plurality of locations. Preferably, depth is determined using an ultrasonic imager. Further preferably, the ultrasonic imager is mounted on the probe.

Preferably, the excavating is performed while the ischemic portion of the heart is in motion.

There is also provided in accordance with a preferred embodiment of the invention, a method of excavating, including, bringing a probe to a location, injecting microbubbles at the location and causing cavitation of tissue at the location using ultrasound. Preferably, the microbubbles are injected directly into the tissue. Alternatively, the microbubbles are injected into the vascular bed of the tissue.

In a preferred embodiment of the invention where the tissue is cancerous, injecting includes injecting microbubbles which perfuse through capillaries in the cancerous tissue at the location.

This is also provided in accordance with another preferred embodiment of the invention, a method of coordinating two probes, including:

(a) providing a first and second probe, each of which has a position sensor mounted thereon;

(b) performing a medical procedure at a location using the first probe;

(c) determining the relative positions of the probes; and (d) performing a medical procedure at the location using the second probe, where the localization of the medical procedure performed by the second probe is based on the determined relative positions.

Preferably, the second probe is an ultrasonic imaging probe and the second probe is oriented to view the location using the determined relative locations.

In a preferred embodiment of the invention, a third probe is provided for assisting the first probe in the medical procedure.

There is further provided in accordance with a preferred embodiment of the invention, a method of coordinating two probes, including:

(a) providing a first and second probe, each of which has a position sensor mounted thereon;

(b) performing a first medical procedure at a first location using the first probe;

(c) performing a second medical procedure at a second location using the second probe;

(d) determining the relative positions of the probes; and (e) coordinating the two medical procedures using the determined relative positions. Preferably, a third medical procedure at a third location is performed using a third probe which is coordinated with the two probes.

Preferably, the relative positions include relative orientations.

Preferably, the second probe is an ultrasonic imaging probe. Additionally or alternatively, the second probe is a vacuuming probe. Additionally or alternatively, the first probe is an evacuating probe. Additionally or alternatively, the second probe is a microbubble injecting probe.

Preferably, determining the relative positions of the probes includes, determining the position of the first probe using non-ionizing radiation, determining the position of the second probe using non-ionizing radiation and subtracting the two positions.

BRIEF DESCRIPTION OF THE DRAWINGS

The invention will be more clearly understood from the following description of preferred embodiments thereof in conjunction with the following drawings in which.

DETAILED DESCRIPTION OF THE PREFERRED EMBODIMENTS

One preferred embodiment of the invention relates to apparatus and means for excavating in the heart, for example, to aid perfusion by making holes in the heart wall.

Figure 1A:
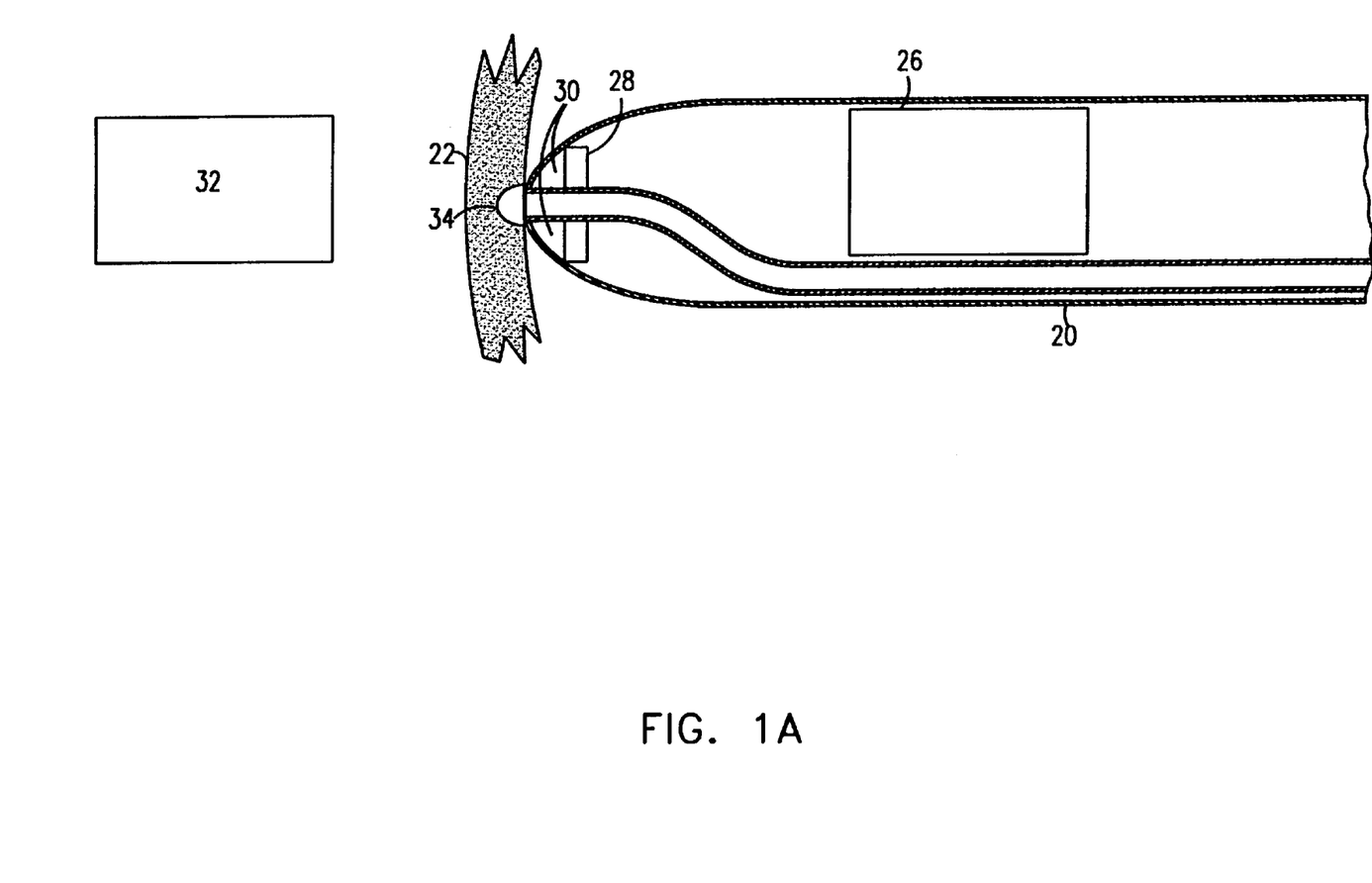
FIGS. 1A–1C show various embodiments of excavating catheters according to preferred embodiments of the invention.

FIG. 1A shows an excavating catheter 20 in contact with a cardiac wall segment 22, according to a preferred embodiment of the invention. Catheter 20 includes means for excavating in segment 22, preferably a laser light source 24 which drills holes in segment 22. Laser source 24 may be a fiber optic fiber connected to an external laser source. Catheter 20 also includes a position sensing device 26, which senses the instantaneous position of the tip of catheter 20. In a preferred embodiment of the invention, position sensor 26 is an AC magnetic field receiver, which senses an AC magnetic field generated by a transmitter 32. Preferred position sensors are further described in U.S. Pat. No. 5,391,199 and in PCT application PCT/US95/01103, published as WO96/05768, the disclosures of which are incorporated herein by reference. Position sensor 26 is preferably used to determine when catheter 20, which is in contact with segment 22, is not in motion. During diastole, the heart is relatively motionless for a short period of time (at most, a few hundred milliseconds). Alternatively to a position sensor, the location of catheter 20 is determined using outside sensing or imaging means. Laser 24 is preferably operated only when catheter 20 is not in motion, assuring that laser 24 only excavates a single localized excavation 34.

In addition to determining absolute motion of catheter 20 it is important to determine relative motion between catheter 20 and excavation 34. Several methods of determining relative motion between catheter 20 and evacuation 34 are described in a U.S. patent application titled "Cardiac Electromechanics", invented by Shlomo Ben-Haim and filed Feb. 1, 1996 and a corresponding U.S. Provisional application No. 60/009,769, the disclosures of which are incorporated herein by reference. The methods disclosed include, determining that catheter 20 repeats the same trajectory every cardiac cycle, determining the existence of motion-induced artifacts in a locally sensed electrogram and determining that catheter 20 stays continuously in contact with segment 22, using a pressure sensor or by measuring impedance between catheter 20 and a body electrode. The above reference U.S. patent application also discloses methods for performing mapping, particularly functional mapping, of internal organs, such as the heart.

In a preferred embodiment of the present invention, position sensor 26 also senses the orientation of catheter 20. Preferably, roll and yaw are sensed, more preferably, pitch is also sensed. Knowing the orientation of catheter 20 results in knowing not only the position of one end of excavation 34 but also its morphology in segment 22. Thus, it is possible to operate laser 24 also when the catheter is in motion, since an exact excavation position can be determined. Further, by operating laser 24 in a controlled manner while catheter 20 is in motion, a wider excavation 34 can be created. Pitch is important if laser 24 is not coaxial with position sensor 26.

In a preferred embodiment of the invention, catheter 20 includes means for deflecting (not shown) the tip of catheter 20, for example, as disclosed in the above referenced PCT application PCT/US95/01103. Alternatively, other catheter tip deflection mechanisms, as known in the art, can be used. By deflecting the tip of catheter 20, it is possible to control the direction of the excavation with more precision. Therefore, small orientation changes of the catheter are correctable. In addition, by moving the tip by a controlled amount, the width of excavation 34 can be controlled.

In preferred embodiment of the invention, catheter 20 is brought into one of the coronary arteries or veins and holes are drilled from the coronary vessel into the heart. Thus, reducing the chance of leakage of blood from the circulation. Optionally, a stent is placed into the hole. By changing the orientation of the tip using the deflecting means, it is possible to choose a preferred excavation direction even in a cramped space such as a coronary vessel.

It should be appreciated that instead of controlling the orientation of the tip of catheter 20, the orientation of laser source 24 relative to the tip of catheter 20 can be controlled using similar means, such as pull wires or other means such as piezoelectric micromotors.

Preferably, an external imaging sensor, such as an echocardiograph (trans-esophageal) is used to provide feedback on the progress of the excavation. In particular, the depth of the excavation is preferably monitored, to reduce the possibility of cardiac perforation.

In a preferred embodiment of the invention, catheter 20 incorporates ultrasonic imager 28 in addition to or instead of position sensor 26. Imager 28 includes a phased array sensor for imaging of tissue in the entire area in front of catheter 20. Alternatively, imager 28 includes a multi-element piezoelectric transducer which transmits a plurality of ultrasound beams directly forward. Alternatively, imager 28 includes a single forward looking piezoelectric transducer. It should be appreciated that in embodiments where laser source 24 excavates in a single direction, in many cases it is sufficient to have a bore-sight view of the surrounding tissue to provide feedback on the excavation. One benefit of using an ultrasonic imager mounted on catheter 20 is that higher ultrasonic frequencies can be used, since attenuation of the signal is not an issue. Usually, higher frequency ultrasound imagers can be implemented in smaller sizes than lower frequency ultrasound. Also, the resolution is usually better.

In a preferred embodiment of the invention portion 30 between segment 22 and ultrasonic imager 28 is filled with an ultrasound coupling medium. Preferably, when laser light from source 24 is provided through the center of ultrasonic imager 28, the medium is transparent to the wavelength of the laser light. Alternatively, laser source 24 is at one side of ultrasonic imager 28. Imager 28 is expediently used to determine the depth and/or width of excavation 34.

In a preferred embodiment of the invention, perfusion in the heart is aided by drilling holes in the heart which do not perforate the heart. Thus, there is less danger to the patient. Preferably, imager 28 is used to determine the tissue type underlying excavation 34 to reduce the possibility of inadvertently damaging a critical cardiac structure. Alternatively or additionally, the location of conduction pathways in the heart are determined from the local electrical activity, which may be measured using an electrode (not shown) on the catheter.

In an additional preferred embodiment of the invention, a thrombosis in a coronary artery is disintegrated using a laser beam. Imager 28 is used to determine whether the thrombosis has been perforated by the laser beam and whether the laser beam is in danger of damaging a portion of the surrounding blood vessel.

In addition, imager 28 can be used to determine that no important anatomical structure, for example, nerve bundles or blood vessels, is in danger of being damaged by the excavation. This determination is especially important when catheter 20 is used outside the heart, in anatomical regions where it is difficult to determine ahead of time what structures lie in the path of the planed excavation. It should be appreciated that in some cases, IR imagers, optical imagers or other types of imagers may be preferable to ultrasonic imagers.

In an additional preferred embodiment of the invention, both laser source 24 and imager 28 are directed at a substantial angle to the long axis of catheter 20. For this configuration, the excavation direction can be easily controlled by rotating catheter 20. One example of such a catheter is a catheter in which laser source 24 is perpendicular to the axis of catheter 20. Use of a position detector for the catheter tip provides the information required to properly direct the laser.

Figure 1B:
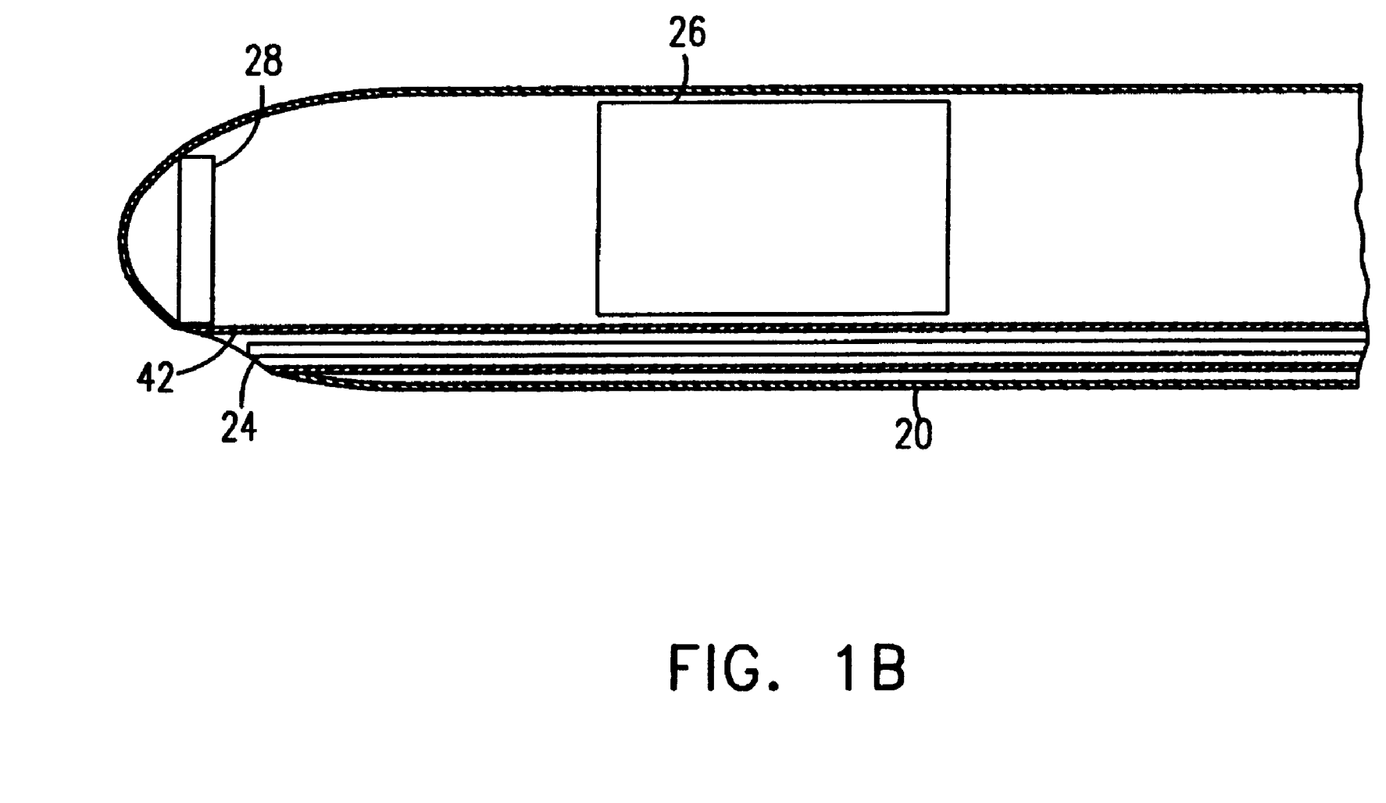

As can be appreciated, excavating using a laser can be very messy. In particular, large pieces of excavated tissue may form thromboses. Also, burnt tissue may accumulate on catheter 20 and block laser source 24. FIG. 1B shows a catheter 20 according to a preferred embodiment of the invention, where a tube 42 conveys washing fluid to the tip of catheter 40. Preferably, tube 42 provides a continuous supply of saline solution to wash away debris from excavation 34. Alternatively, tube 42 is used as a vacuum cleaner to remove debris from the vicinity of excavation 34. In a further preferred embodiment of the invention, both washing and vacuuming functions are provided by two separate tubes at the tip of catheter 40. Preferably, vacuuming takes place during excavating.

Although laser light is highly controllable, it is not suitable for all types of excavations. Laser light tends to drill long and narrow bores, if a wide and shallow excavation is desired, very short laser pulses must be applied at a plurality of locations. Focused ultrasound can cause tissue damage by one of two mechanisms, local heating and cavitation. Local heating damages most tissues and especially tumors. Cavitation damages all types of tissue, essentially liquefying them by causing tissue cells to explode. A major limitation of focused ultrasound is the current technical inability to form small focal areas in the order of several millimeters.

In a preferred embodiment of the invention, microbubbles are provided in a tissue to be destroyed and the tissue is irradiated with high power ultrasound, such as focused ultrasound. Microbubbles are many times more sensitive to cavitation than regular tissue due to the tiny gas bubbles encapsulated within them, so relatively low intensities of ultrasound will cause cavitation in microbubble-containing tissue and will not damage microbubble-free tissue. Thus, the effective resolution of focused ultrasound techniques is increased; only tissue which is irradiated with focused ultrasound and which contains microbubbles will be affected by the focused ultrasound. An addition benefit of using microbubbles is that lower energy levels are required to form cavitation, making it more practical to apply focused ultrasound through the rib cage or to provide a focused ultrasound source at a tip of a catheter. A still further benefit of using microbubbles is that microbubbles are very visible on ultrasound images, thus providing a contrast enhancing agent for catheter-mounted ultrasound transducers which may be used to determine the expected excavation area. Yet another advantage of evacuation using microbubbles is in moving organs. Since substantially only microbubble-containing tissue is affected by the focused ultrasound, it is not necessary to track the excavation area with the focused ultrasound beam. Rather, it is sufficient that the focused ultrasound beam intersect microbubble-containing tissue for a significant percentage of time. Preferably, lipid coated microbubbles, such as described in U.S. Pat. No. 5,215,680 are used. Alternatively, an emulsified suspension of gas bubbles in water is used.

Figure 1C:
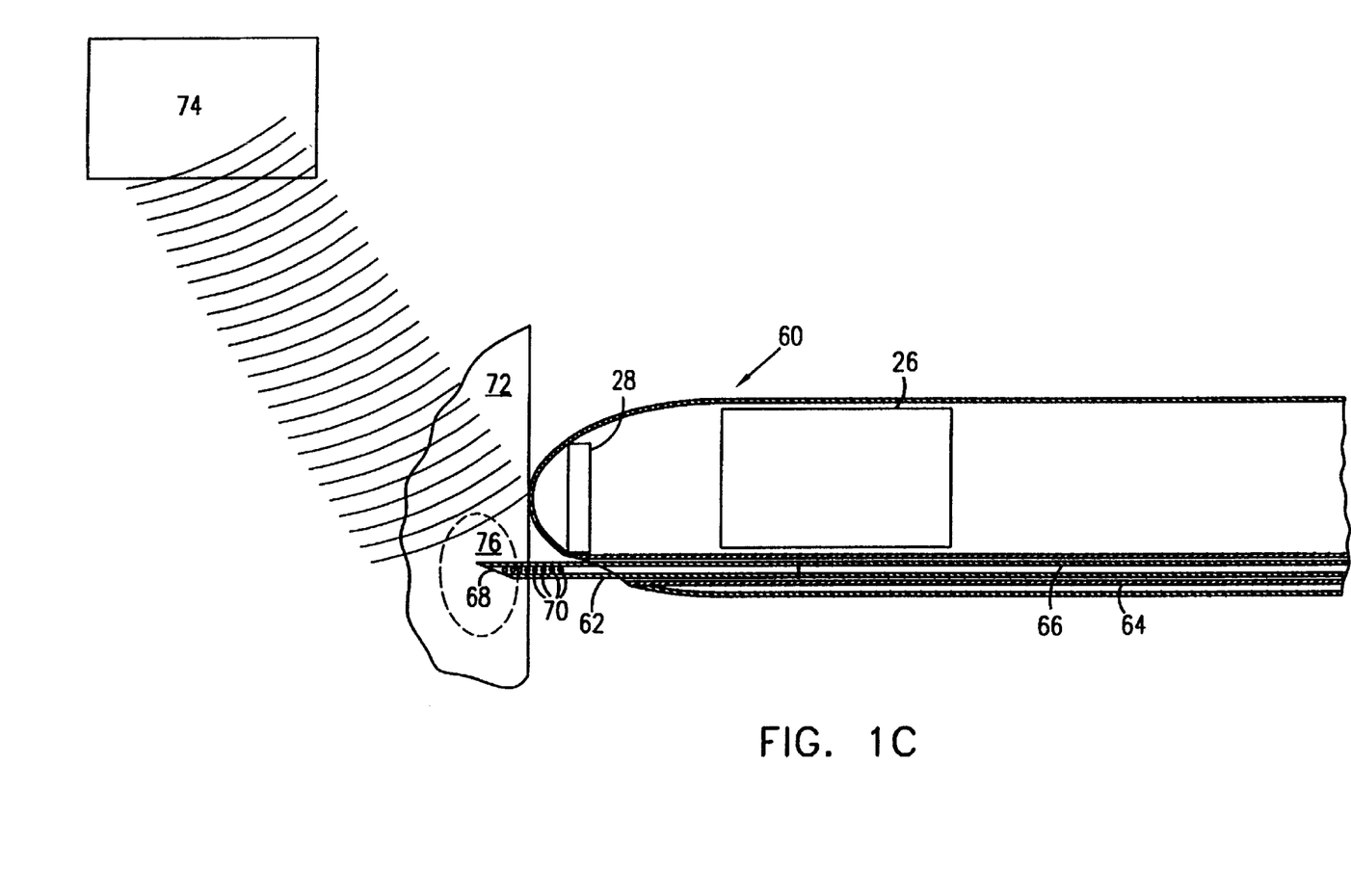

One method of providing microbubbles in a tissue portion is to inject microbubbles into the tissue. FIG. 1C shows a catheter 60 having a needle 62 for injecting microbubbles into adjacent tissue, according to a preferred embodiment of the invention. A tube 64 transports microbubbles from outside the body to needle 62. In operation, needle 62 is inserted into a tissue portion 76 and microbubbles are injected through a hole 68 at the distal end of needle 62. Alternatively or additionally, microbubbles are injected through a plurality of holes 70 at the sides of needle 62. Alternatively, needle 62 is used to inject gas bubbles, such as carbon dioxide, instead of injecting microbubbles. An advantage of carbon dioxide is that it rapidly dissolves in the blood, so that it does not cause prolonged occlusion of capillaries.

A ultrasound generator 74, for example a focused ultrasound generator, irradiates tissue 72 which includes microbubble-containing tissue 76 and causes cavitation in tissue 76.

Needle 62 may be moved out of catheter 60 and into tissue 76 by pressurizing tube 64 with a micro-bubble containing fluid. Microbubbles ejected from needle 62 when needle 62 is not in tissue 76 will be carried away by the blood stream. Alternatively, needle 62 can be urged forward and backward using a using a guide 66. Preferably, guide 66 is hollow so that microbubbles can be transported through guide 66.

Figure 2:
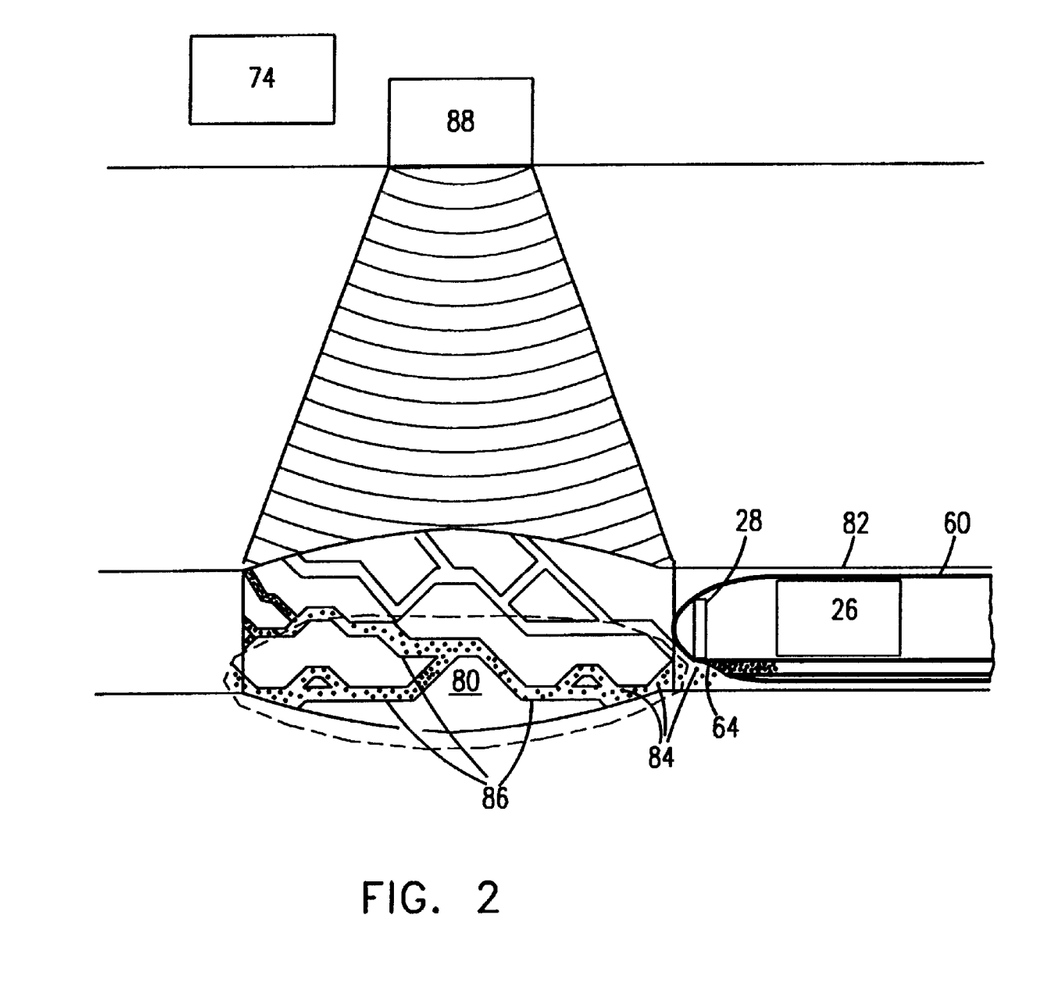
FIG. 2 illuminates a method of injecting microbubbles into specific capillaries so that a desired tissue portion can be destroyed by cavitating the microbubbles, according to a preferred embodiment of the invention.

FIG. 2 illuminates a method of microbubble-assisted excavation in which microbubbles 84 are conveyed to a tissue portion 80 to be destroyed using capillaries 86 in tissue 80. Catheter 60, preferably without an injection needle such as shown in FIG. 1C, injects microbubbles 84 into an artery 82 which leads to capillaries 86. The artery is chosen such that the extent of tissue 80 is equal to the area perfused by vessel 82. The size and location of tissue 80 can be controlled by choosing a different artery 82. It should be appreciated, that if catheter 60 has position sensor 26 mounted thereon, navigating to a particular vessel 82 is relatively easy and does not require the use of a fluoroscope. When the tissue to be cavitated is cancerous tissue, there is an additional benefit. As described above, capillaries in cancerous tissue are permeable to microbubbles, while capillaries in normal tissues are not. As a result, the microbubbles accumulate in the cancerous tissue and not only in the capillaries, further increasing the relative sensitivity of cancerous tissue.

One advantage of infusing microbubbles through the capillaries is that the microbubbles leave tissue 80 after a short while. The flow in the capillaries is relatively slow, so there is a significant time period during which capillaries 86 are infused with microbubbles. However, after a while capillaries 86 clear. Larger microbubbles tend to clog capillaries, so the time period where capillaries 86 are infused with micro bubbles can be controlled by using different sizes of microbubbles. In operation, catheter 60 releases microbubbles 84 into vessel 84. Focused ultrasound transmitter 74 irradiates a tissue portion including tissue portion 80. Preferably, the existence of microbubbles in portion 80 is ascertained using an ultrasound scanner 88. Alternatively, ultrasonic imager 28 on catheter 60 are used to ascertain the existence of microbubbles in tissue portion 80.

One problem with focused ultrasound is that, due to non-uniformities in the velocity of sound in soft tissue, the actual focus point may be different from the planned focal point. In a preferred embodiment of the invention, which does not necessarily utilize microbubbles, ultrasonic imager 28 that is mounted on catheter 60, is used to determine the amplitude and/or phase of the focused ultrasound. In one preferred embodiment of the invention, a probe, such as needle 62 (FIG. 1B), is used to convey ultrasound energy from the region to be excavated to ultrasonic imager 28.

Figure 3:
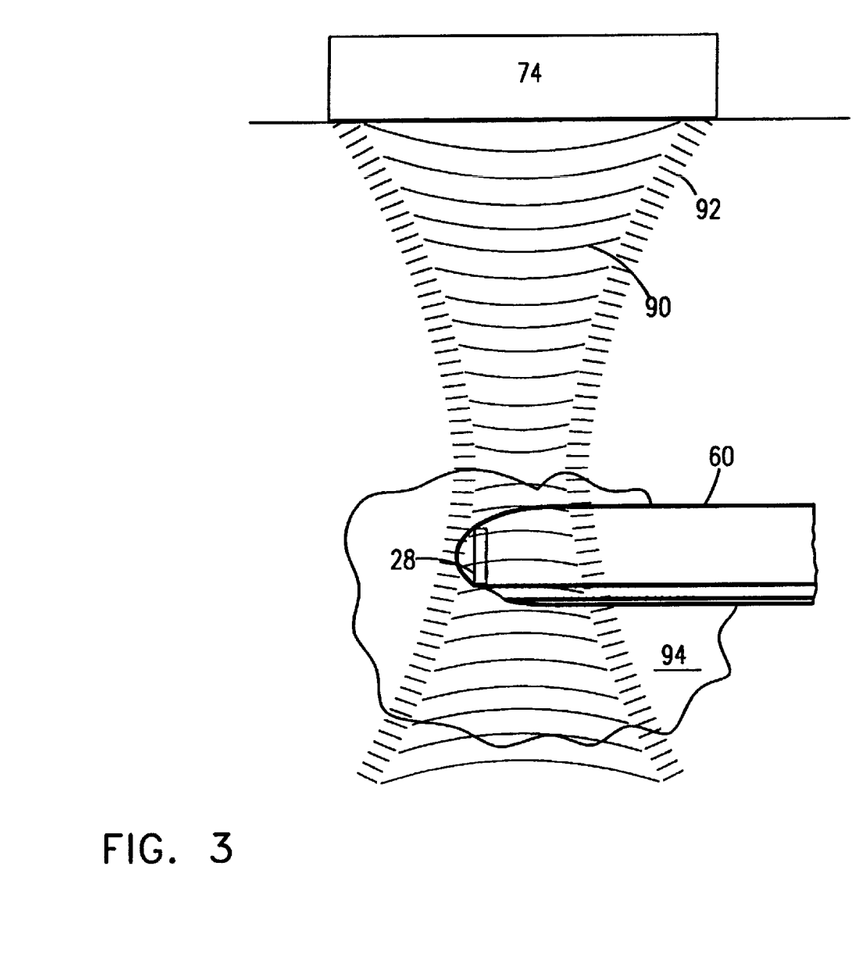
FIG. 3 illuminates a method of aiming focused ultrasound using a catheter.

FIG. 3 illuminates a method of directing the aim of a focused ultrasound beam. Transmitter 74 transmits an ultrasound beam having an inner portion 90 which is differentiable, e.g., by frequency, from an outer portion 92 of the beam. Catheter 60 is brought to a region 94 which is the planned focal point of transmitter 74 and senses, using imager 28, whether the focused ultrasound beam is correctly aimed and focused. A controller (not shown) may be used to change the focusing and localization of the focused ultrasound beam so that it is correctly aimed. As can be appreciated, imager 28 may be an ultrasonic sensor instead of an imager.

In another preferred embodiment of the invention, a catheter is brought to a lesion in a minimally invasive manner mostly through the vascular system. When the catheter is in the vicinity of the lesion, the catheter is urged through the wall of the blood vessel and towards the lesion. As can be appreciated, a positioning sensor is very helpful in navigating outside of the vascular system. Also, a forward looking ultrasound imager, such as ultrasonic imager 28 is useful to determine that the forward motion of the catheter will not damage important anatomical structures. Ultrasonic imaging forward of the catheter can also be used to navigate the catheter towards a specific lesion.

One way of tunneling through tissue is to simply force the catheter forward and steering is preferably accomplished by changing the orientation of the catheter tip. It should be appreciated that most portions of the body are no more than 2 or 3 centimeters from a blood vessel or body cavity with a diameter of 3 or 4 millimeters (i.e., large enough for catheterization). When catheterizing the brain, it is important to note that the shortest distance between two points might pass through a particularly important portion of the brain. Therefore, the actual path along which the catheter is urged will depend greatly on the location of the lesion relative to important brain structures.

Another way of tunneling through tissue is to provide the catheter with a, preferably retractable, cutting tip which cuts through flesh. Preferably, ultrasonic imager 28 are used to determine the orientation of tissue fibers adjacent the tip of the catheter. The catheter is then rotated so that the cutting tip will cut in parallel to the tissue fiber and not across them. This is especially important when cutting through muscle fiber, since parallel cuts heal much faster than cross-cuts.

Still another way of tunneling through tissue is to inject tissue dissolving chemicals into the tissue adjacent the tip of the catheter. Tissue solvents can be of a type which destroys tissue, or more preferably, of a type which only dissolves connective tissues. Preferably, the tissue solvent is mixed with a small amount of microbubbles so that ultrasonic imager 28 can determine that the tissue solvent was injected into the right area.

In addition, tunneling through tissue can be achieved by excavating tissue adjacent to the catheter tip as described herein above.

It should be appreciated that apparatus and methods as described above can be used to inject therapeutical agents anywhere in the body. It should be further appreciated, that a catheter which has a position sensing device can be navigated using a real-time reference image (which may or may not show the catheter), a previously taken reference image or even with no reference image at all.

A liver shunt operation using the above described methods and apparatus includes:

(a) bringing a first catheter into the hepatic vein;
(b) determining the location of the portal vein, either using ultrasound;
(c) tunneling from the hepatic vein to the portal vein, either by forcing the catheter through the intervening tissue or by destroying the intervening tissue using a laser of microbubble-assisted focused ultrasound; and
(d) installing a stent between the two veins.

A lesion, such as a tumor or a cyst, practically anyplace in the body can be removed by bringing the catheter to the lesion and excavating the lesion as described above. Preferably, the debris is removed from the body through the catheter.

Although the above methods and apparatus have been mainly described as operating in and through the vascular system, the methods and apparatus can be used in any body cavity, such as the digestive system and the respiratory system. In addition, a catheter can be inserted directly into the body tissue, like a laproscope.

In many cases it is not practical to use catheters having several different tools at their tips. One reason is the high cost of complex catheters; another reason is that some tools interfere with the operation of other tools; and a further reason is that multi-tool catheters generally have a larger diameter than single tool catheter, and as such, are more limited in their reach and flexibility. One common solution is to provide a catheter with a lumen. A single tool is guided through the lumen to the tip of the catheter and when a different tool is needed the tool is replaced.

Figure 4A:
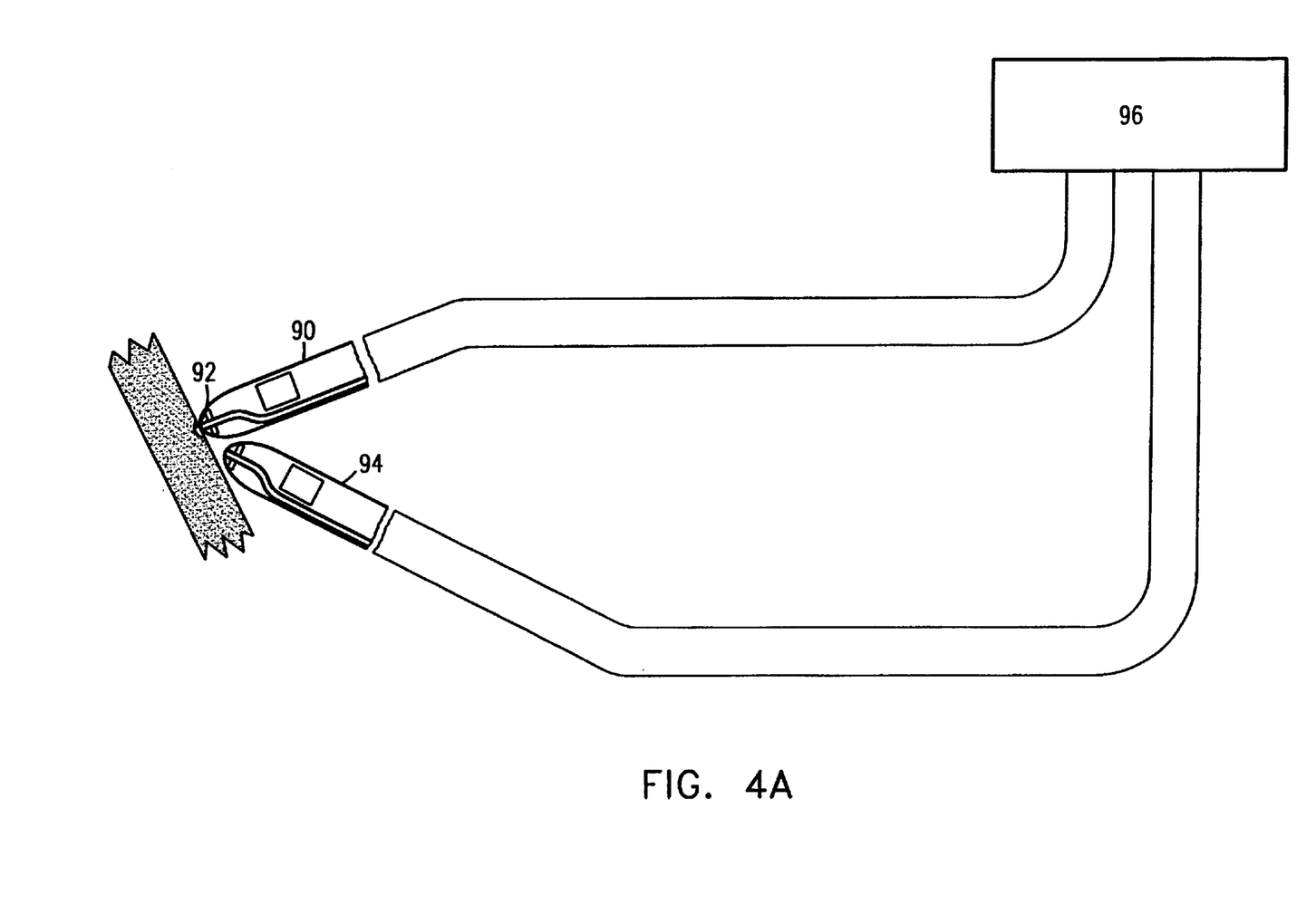
FIGS. 4A–4C shows examples of catheter surgery using a plurality of coordinated catheters, according to preferred embodiments of the invention.

In a preferred embodiment of the invention a plurality of one-tool catheters are coordinated through the use of position sensors mounted on at least some of the catheters. FIG. 4A shows a catheter 90 excavating at a location 92 and a ultrasonic imaging catheter 94, which looks at location 92. Preferably, a controller 96 controls the viewing direction of catheter 94 so that it is always viewing location 92 and/or catheter 90.

As can be appreciated, in many cases it is not the exact position of the catheters, but their relative position which is important. For example, the exact position of catheter which are in the heart is almost never important because the heart is almost continuously in motion.

Figure 4B:
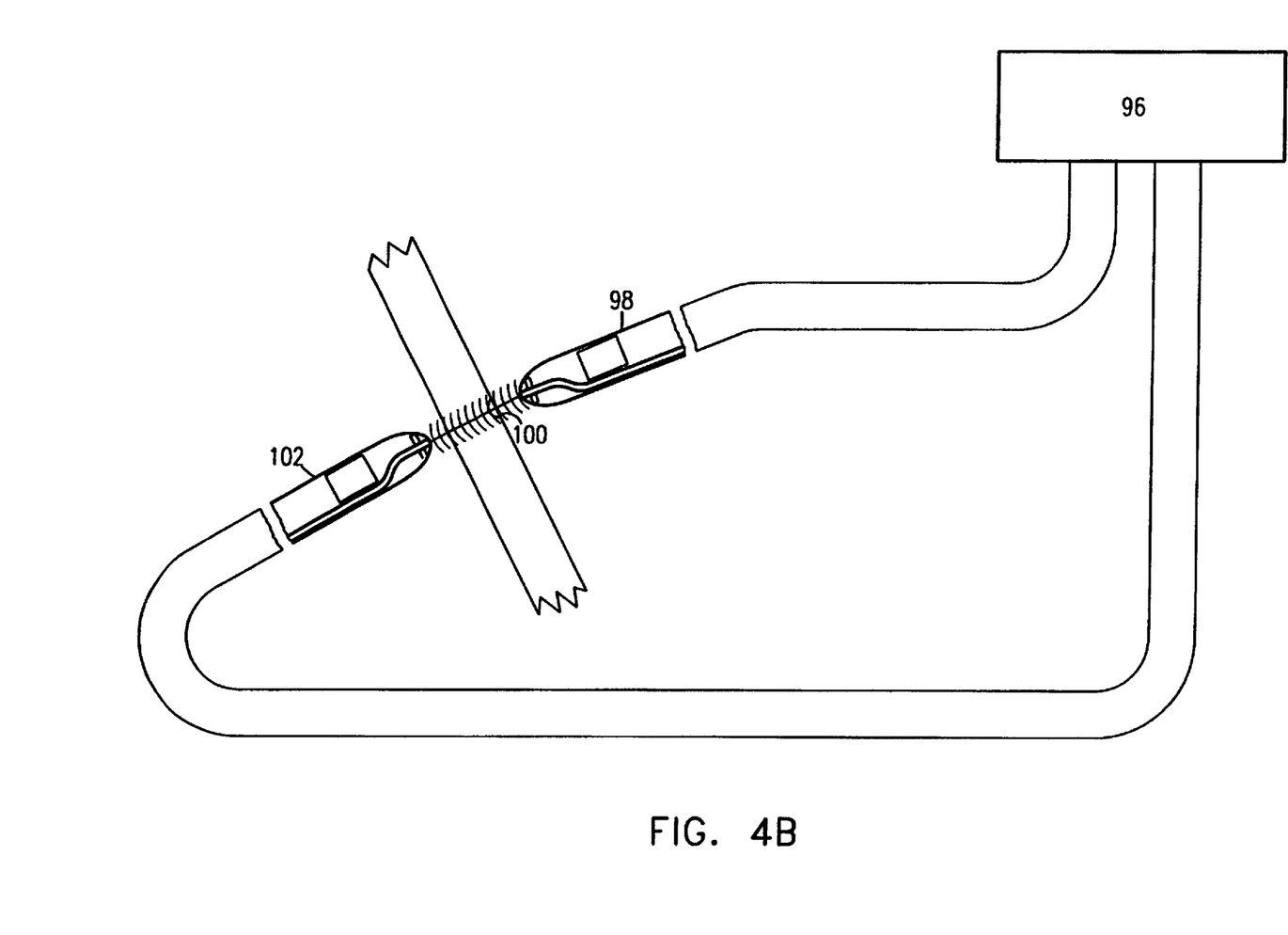

FIG. 4B shows a catheter 98 which transmits ultrasound signals to a location 100, so that a catheter 102, which receives ultrasonic signals can view location 100.

Figure 4C:
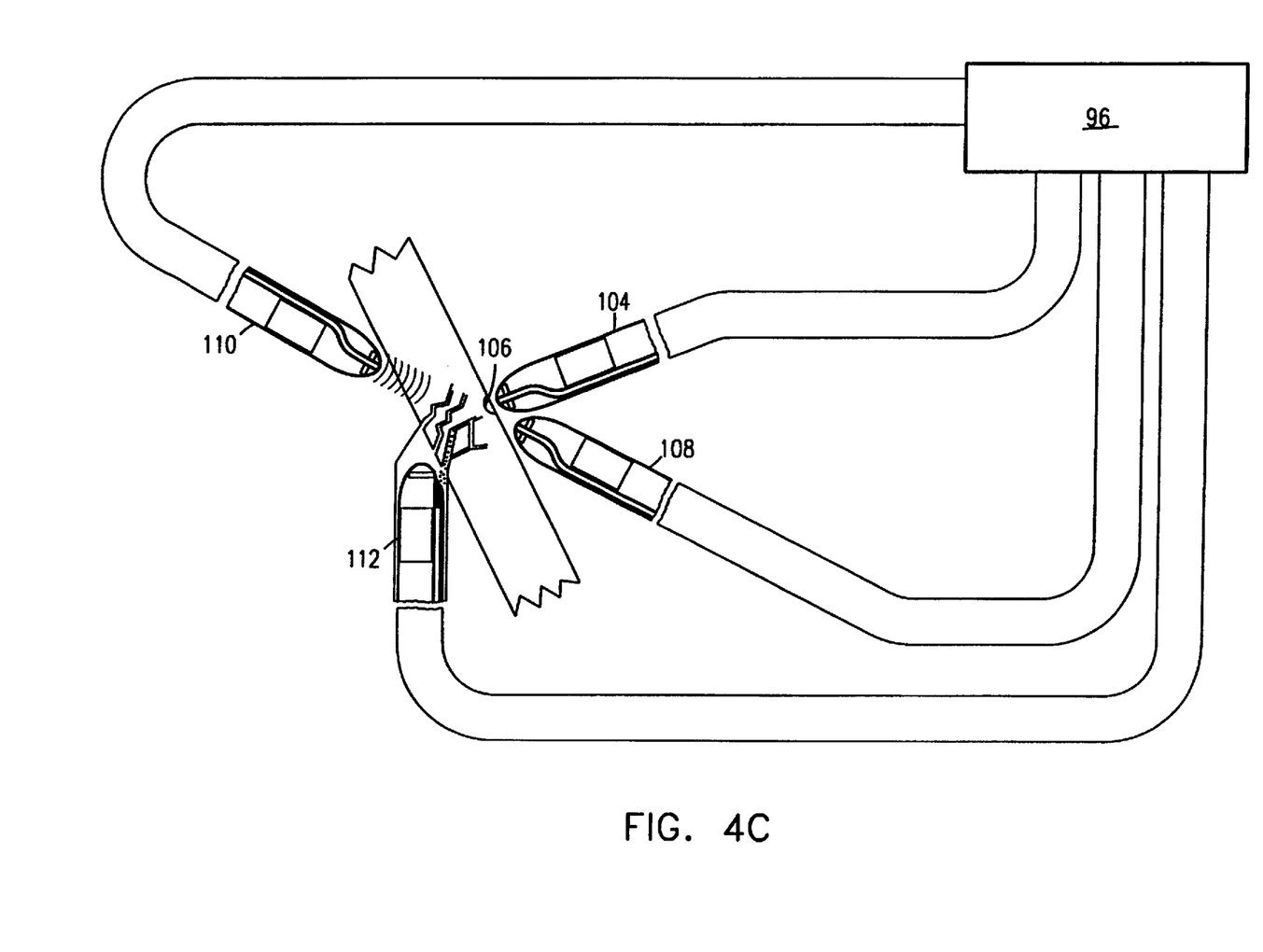

FIG. 4C shows a four catheter scenario, in which a catheter 104 is excavating at a location 106, a catheter 108 is removing the debris, a catheter 110 is viewing the tissue surrounding location 106 and a catheter 112 is injecting microbubbles into the vascular bed of location 106 to enhance the contrast between different types of tissue at location 106.

The invention has thus far been illustrated using non-limiting examples. It will be appreciated by a person skilled in the art the present invention is not limited to what has been described. In particular, many variations of the described apparatus and the described medical procedures are applicable within the scope of the invention, which is limited only by the claims which follow.

What is claimed is:

1. An excavating probe for use in a generated magnetic field comprising:
    (a) a probe body having a distal tip;
    (b) a position sensor near the distal tip, the position sensor being a magnetic field receiver which determines the position of the tip by sensing the instantaneous position of the tip from a generated magnetic field; and
    (c) a source of microbubbles at the tip.

2. A probe according to claim 1, wherein the source of microbubbles comprises a hollow needle which injects the microbubbles into tissue adjacent the tip.

3. A probe according to claim 2, comprising an ultrasonic imager which views regions adjacent said tip.

4. A probe according to claim 2, wherein the position sensor comprises an orientation sensor which determines the orientation of the tip of the probe.

5. A method of excavating within a generated magnetic field comprising:
    (a) bringing a probe to a location, the probe comprising a probe body having a distal tip, a position sensor near the distal tip wherein the position sensor is a magnetic field receiver which determines the position of the tip by sensing the instantaneous position of the tip from a generated magnetic field and a source of microbubbles;
    (b) injecting microbubbles at the location; and
    (c) causing cavitation of tissue at the location using ultrasound.

6. A method according to claim 5, wherein (b) comprises, injecting microbubbles directly into tissue at the location.

* * * * *